United States Patent
Helpenstein et al.

(10) Patent No.: US 10,273,335 B2
(45) Date of Patent: Apr. 30, 2019

(54) TITANIUM COMPLEXES AS VULCANIZATION CATALYSTS

(71) Applicant: Henkel AG & Co. KGaA, Duesseldorf (DE)

(72) Inventors: Klaus Helpenstein, Moenchengladbach (DE); Johann Klein, Duesseldorf (DE); Andrea Gutacker, Duesseldorf (DE); Esteban Mejia, Rostock (DE); Steve Hillbrandt, Rostock (DE); Udo Kragl, Kritzmow (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 54 days.

(21) Appl. No.: 15/371,555

(22) Filed: Dec. 7, 2016

(65) Prior Publication Data

US 2017/0081479 A1    Mar. 23, 2017

Related U.S. Application Data

(63) Continuation of application No. PCT/EP2015/064546, filed on Jun. 26, 2015.

(30) Foreign Application Priority Data

Jun. 26, 2014  (DE) .................. 10 2014 212 291

(51) Int. Cl.

| | |
|---|---|
| C08G 77/08 | (2006.01) |
| C07F 7/28 | (2006.01) |
| C08G 77/18 | (2006.01) |
| C09J 183/04 | (2006.01) |
| C08G 77/26 | (2006.01) |
| C09J 183/06 | (2006.01) |
| C09J 183/08 | (2006.01) |
| C08K 5/00 | (2006.01) |
| C08G 77/16 | (2006.01) |

(52) U.S. Cl.
CPC ............ *C08G 77/08* (2013.01); *C07F 7/28* (2013.01); *C08G 77/18* (2013.01); *C08G 77/26* (2013.01); *C09J 183/04* (2013.01); *C09J 183/06* (2013.01); *C09J 183/08* (2013.01); *C08G 77/16* (2013.01); *C08K 5/0025* (2013.01)

(58) Field of Classification Search
CPC .............................. C08G 77/18; C08K 5/0091
See application file for complete search history.

(56) References Cited

U.S. PATENT DOCUMENTS

| | | | |
|---|---|---|---|
| 4,530,882 A | 7/1985 | Homan et al. | |
| 5,286,766 A | 2/1994 | Arai et al. | |
| 5,948,854 A | 9/1999 | De Buyl et al. | |

FOREIGN PATENT DOCUMENTS

| | | | |
|---|---|---|---|
| CN | 102513156 | 6/2012 | |
| EP | 0520426 | 12/1992 | |
| EP | 0747443 | 12/1996 | |
| EP | 0853101 | 7/1998 | |
| EP | 1746135 | 1/2007 | |
| JP | 2005 213487 | * | 8/2005 |
| WO | 2013/036546 | 3/2013 | |

OTHER PUBLICATIONS

JP 2005 213487 machine translation (2005).*
International Search Report issued.

* cited by examiner

*Primary Examiner* — Kuo Liang Peng
(74) *Attorney, Agent, or Firm* — James E. Piotrowski

(57) ABSTRACT

The invention relates to a curable composition comprising: a) at least one polymer having at least one silicon-containing group of formula —Si($R^1$)$_k$(Y)$_{3-k}$ as defined herein; b) at least one titanium compound of formula Ti(L)$_n$(NX$_2$)$_m$ or Ti($R^3$)(L)$_3$, where each X is independently a hydrogen atom, a hydrocarbon radical containing 1 to 20 C atoms, which may optionally contain one or more heteroatoms, in particular nitrogen atoms, or a silicon-containing organic group, or two X together with the nitrogen atom to which they are bound form a heterocyclic ring; each L is independently a hydrolyzable oxygen- or nitrogen-containing organic group, in particular an alkoxy group; $R^3$ is a hydrocarbon radical containing 1 to 20 C atoms, which may optionally contain one or more heteroatoms, in particular silicon atoms; and m is 1, 2, 3, or 4 and and n is 0, 1, 2, or 3, where m+n=4; and c) optionally at least one compound which has a hydrolyzable silicon-containing group and a molecular weight in the range of 100 to 1000 g/mol, preparations containing these compositions and use thereof.

15 Claims, No Drawings

TITANIUM COMPLEXES AS VULCANIZATION CATALYSTS

The invention relates to titanium compounds which are useful as catalysts for the vulcanization of silicon-containing polymers and polymer mixtures, and which may replace known, toxic tin compounds. The described titanium compounds are characterized by good catalytic activity and stability, even in the presence of silane-based adhesion promoters. In addition, suitable uses for such compounds and compositions and preparations containing these catalysts are described.

Silicone polymers, in particular polymethylsiloxanes such as polydimethylsiloxane (PDMS), are of great importance in adhesives, sealants, and insulating materials. Among these materials, those which vulcanize at low temperatures and under ambient conditions constitute a considerable market share. Typical formulations contain a reactive PDMS polymer, a crosslinker, and a condensation catalyst. Although organotin compounds have been successfully used as catalysts for many years and produce excellent results with regard to storage stability, curing time, and selectivity, they have come under criticism in recent times due to toxicological concerns and for reasons of environmental protection.

Although various metal-based catalysts have been proposed as a replacement for the known tin compounds, the known alternatives often have disadvantages with regard to stability, catalytic activity, or compatibility. Thus, the titanium compounds known as a replacement have the disadvantage, for example, that they are not compatible with the aminosilanes frequently used as adhesion promoters.

Curable silicone compositions which contain siloxane polymers having hydrolyzable end groups, titanium-based hydrolysis catalysts, and optionally aminosilanes are known from U.S. Pat. Nos. 4,530,882 A, 5,948,854 A, and 5,286,766 A. The titanium-based hydrolysis catalysts are titanium esters, preferably tetraalkyl titanates, particularly preferably tetraisopropyl titanate. These catalysts as well are not completely satisfactory with regard to their catalytic activity. In addition, the storage stability of corresponding curable compositions is not optimal, and the cured products obtainable therefrom have comparatively low hardness.

It is therefore an object of the present invention to provide alternatives to the titanium compounds known as condensation catalysts, which overcome the known disadvantages.

The present invention achieves the object of providing improved condensation catalysts based on titanium for use for curing polymers containing reactive silicon groups, which meet the above-described requirements, i.e., which have sufficient catalytic activity and stability and which are compatible with the aminosilanes customarily used as adhesion promoters.

In a first aspect, the invention therefore relates to a curable composition comprising a) at least one polymer having at least one silicon-containing group of formula (1)

$$—Si(R^1)_k(Y)_{3-k} \qquad (1),$$

where $R^1$ is a hydrocarbon radical containing 1 to 20 C atoms or a triorganosiloxane group of formula —O—Si($R^2$)$_3$, where each $R^2$ is independently a hydrocarbon radical containing 1 to 20 C atoms;
each Y is independently a hydroxy group or a hydrolyzable group, in particular an oxime group and/or alkoxy group; and
k is 0, 1, or 2;

b) at least one titanium compound of formula (2)

$$Ti(L)_n(NX_2)_m \qquad (2)$$

or of formula (3)

$$Ti(R^3)(L)_3 \qquad (3),$$

where each X is independently a hydrogen atom, a hydrocarbon radical containing 1 to 20 C atoms, which may optionally contain one or more heteroatoms, in particular nitrogen atoms, or a silicon-containing organic group, or two X together with the nitrogen atom to which they are bound form a heterocyclic ring;
each L is independently a hydrolyzable oxygen- or nitrogen-containing organic group, in particular an alkoxy group;
$R^3$ is a hydrocarbon radical containing 1 to 20 C atoms, which may optionally contain one or more heteroatoms, in particular silicon atoms; and m is 1, 2, 3, or 4 and n is 0, 1, 2, or 3, where m+n=4; and c) optionally at least one compound which has a hydrolyzable silicon-containing group and a molecular weight in the range of 100 to 1000 g/mol, in particular an aminosilane.

In a further aspect, the invention relates to a preparation which contains a curable composition as described above.

The invention is further directed to the use of a composition or a preparation as defined above as an adhesive or sealant.

Yet a further aspect relates to titanium compounds of formula (6)

$$Ti(OR^4)_3(NXX') \qquad (6),$$

where each $R^4$ is independently $C_{1-8}$ alkyl, in particular for ethyl, isopropyl, or n-butyl; X is hydrogen, $C_{1-20}$ alkyl or aryl, wherein the alkyl radical may optionally contain one or more nitrogen atoms, or a silicon-containing organic group of formula —(CH$_2$)$_p$—Si(Alk)$_q$(OAlk)$_r$, where p is an integer from 0 to 9, q is 0, 1, or 2, and r is 1, 2, or 3, where q+r=3, and Alk is a $C_{1-4}$ alkyl group, in particular methyl or ethyl; and X' is a silicon-containing organic group of formula —(CH$_2$)$_p$—Si(Alk)$_q$(OAlk)$_r$, where p is an integer from 1 to 9, in particular 3, q is 0, 1, or 2, in particular 0, and r is 1, 2, or 3, in particular 3, where q+r=3, and Alk is a $C_{1-4}$ alkyl group, in particular methyl or ethyl.

Lastly, the invention is further directed to the use of the above-described titanium compounds as a catalyst, in particular for curing a silicon-containing polymer by forming siloxane bonds.

When mention is made in the present patent application to molecular weights, unless stated otherwise the reference is to the weight average, i.e., the $M_w$ value, and not the arithmetic average. The molecular weight is determined by gel permeation chromatography (GPC) with tetrahydrofuran (THF) as eluent in accordance with DIN 55672-1:2007-08, preferably at 35° C.

"At least one," as used herein, means 1 or more, i.e., 1, 2, 3, 4, 5, 6, 7, 8, 9, or more. With reference to an ingredient, the indication refers to the type of ingredient and not to the absolute number of molecules. "At least one polymer" thus means, for example, at least one type of polymer, i.e., that one type of polymer or a mixture of several different polymers may be used. Together with the weight indication, the indication refers to all compounds of the stated type which are contained in the composition/mixture, i.e., that the composition contains no further compounds of this type besides the stated quantity of the compounds in question.

Unless explicitly stated otherwise, all percent values provided in conjunction with the compositions described herein refer to % by weight, in each case based on the mixture in question.

There are no special limitations on the polymer backbone of the at least one polymer a), and all known polymers having various types of main chain backbones may be used. In various embodiments, polymer a) is therefore selected from alkyd resins, (meth)acrylates and (meth)acrylamides and the salts thereof, phenolic resins, polyalkylenes, polyamides, polycarbonates, polyols, polyethers, polyesters, polyurethanes, vinyl polymers, siloxanes, and copolymers composed of at least two of the above-mentioned polymer classes.

Polyols/polyethers, in particular polyethylene oxide and/or polypropylene oxide, or siloxanes are particularly preferably used.

According to another preferred embodiment of the composition according to the invention, the molecular weight $M_n$ of the polymer backbone is between 500 and 100,000 g/mol. Molecular weight ranges of 5000 to 25,000 g/mol are particularly preferred, and of 8000 to 20,000 g/mol are very particularly preferred. These molecular weights are particularly advantageous, since compositions with these molecular weights have viscosities which facilitate processing. The polymers may be straight-chain or branched in each case.

The silicon-containing group in the polymer is a reactive group in which a hydroxy group or a hydrolyzable group is bound to the silicon atom, and which is capable of crosslinking by forming a siloxane bond. This crosslinking reaction may be accelerated by a silanol condensation catalyst, such as the titanium compounds described herein.

The reactive group has the formula —Si($R^1$)$_k$(Y)$_{3-k}$, where $R^1$ is a hydrocarbon radical containing 1 to 20 C atoms, or a triorganosiloxane group of formula —O—Si($R^2$)$_3$, where each $R^2$ is independently a hydrocarbon radical containing 1 to 20 C atoms, each Y is independently a hydroxy group or a hydrolyzable group, and k is 0, 1, or 2. In various embodiments, $R^1$ is an alkyl group containing 1 to 20 C atoms, an aryl group containing 6 to 20 C atoms, an aralkyl group containing 7 to 20 C atoms, or a triorganosiloxane group of formula —O—Si($R^2$)$_3$ as defined above. If multiple Y radicals are contained, these may be the same or different.

Examples of hydrolyzable groups include but are not limited to a hydrogen atom, a halogen atom, an alkoxy group, an acyloxy group, an oxime group, an amino group, an amide group, an acid amide group, an aminoxy group, a mercapto group, an alkenyloxy group, and the like. Alkoxy groups, in particular methoxy and ethoxy groups, and oxime groups are particularly preferred. The term "oxime groups" as used herein includes ketoximes and aldoximes, and refers in general to groups which contain the functional group $R'_2C=N-O-$, wherein the oxygen atom is bound to the silicon atom, and R' may be H or another group, preferably an alkyl group.

Examples of $R^1$ in general formula (1) described above include alkyl groups, such as a methyl group and an ethyl group, cycloalkyl groups, such as a cyclohexyl group, aryl groups, such as a phenyl group, aralkyl groups, such as a benzyl group, and a trimethylsiloxy group.

Specific examples of reactive silicon-containing groups include dimethoxymethylsilyl, diethoxymethylsilyl, and diisopropoxymethylsilyl groups.

In various embodiments, one polymer molecule in each case contains two or more of the above-described reactive groups.

Methods for inserting reactive silicon-containing groups, preferably end groups, into polymers are well known in the prior art.

The reactive silicon-containing group may be situated on one or both ends of the main chain, within the main chain, or within or on the end of one or more side chains.

As polymer component a), the above-described organic polymers may be used in each case either alone or in combinations of two or more thereof. If combinations of two or more polymers are used, the polymers that are used may differ in their monomer composition and/or their molecular weight.

The curable compositions described herein contain at least one titanium compound of formula (2)

$$Ti(L)_n(NX_2)_m \quad (2)$$

or of formula (3)

$$Ti(R^3)(L)_3 \quad (3),$$

where each X is independently a hydrogen atom, a hydrocarbon radical containing 1 to 20 C atoms, which may optionally contain one or more heteroatoms, in particular nitrogen atoms, or a silicon-containing organic group. X is preferably hydrogen, $C_{1-20}$ alkyl, or $C_{6-20}$ aryl, wherein the alkyl radical may optionally contain one or more nitrogen atoms, or a silicon-containing organic group of formula —(CH$_2$)$_p$—Si(Alk)$_q$(OAlk)$_r$, where p is an integer from 0 to 9, q and r in each case are 0, 1, 2, or 3, where q+r=3, and Alk is a $C_{1-4}$ alkyl group, in particular methyl or ethyl. Alternatively, two X together with the nitrogen atom to which they are bound form a heterocyclic ring. In such embodiments, the heterocyclic ring may be a saturated, singly or multiply unsaturated or aromatic 5- to 8-membered ring containing 1 to 3 heteroatoms, in particular nitrogen, oxygen, or sulfur, preferably nitrogen.

In formulas (2) and (3), each L is independently a hydrolyzable oxygen- or nitrogen-containing organic group, in particular an alkoxy group.

$R^3$ is a hydrocarbon radical containing 1 to 20 C atoms, which may optionally contain one or more heteroatoms, in particular silicon atoms.

In formula (2), m is 1, 2, 3, or 4 and n is 0, 1, 2, or 3, with the condition that m+n=4. It is preferred that m is 1 or 2, in particular 1.

In various embodiments of the invention, the at least one titanium compound is a titanium compound of formula (4)

$$Ti(OR^4)_3(NX_2) \quad (4),$$

where each $R^4$ is independently $C_{1-8}$ alkyl, in particular for ethyl, isopropyl, or n-butyl, and each X is independently hydrogen, $C_{1-20}$ alkyl, or $C_{6-20}$ aryl, wherein the alkyl radical may optionally contain one or more nitrogen atoms, or a silicon-containing organic group of formula —(CH$_2$)$_p$—Si(Alk)$_q$(OAlk)$_r$, where p is an integer from 0 to 9, q and r in each case are 0, 1, 2, or 3, where q+r=3, and Alk is a $C_{1-4}$ alkyl group, in particular methyl or ethyl.

Examples of the (NX$_2$) group include but are not limited to dialkylamido, wherein the alkyl radicals are preferably $C_{1-4}$ alkyl radicals, in particular diethylamido.

In preferred embodiments of the titanium compounds of formulas (2) and (4) described herein, the ligand of formula (NX$_2$) is a ligand that is obtainable by coupling an aminosilane to the titanium. Examples of such ligands include but are not limited to bis(trialkylsilyl)amido, such as bis(trimethylsilyl)amido, trialkoxysilaneamido, and bis(trialkoxysilane)amido, in particular trialkoxysilanealkylamido and bis(trialkoxysilanealkyl)amido, such as 3-(triethoxysilyl)propyl-1-amido (4a), 3-(trimethoxysilyl)propyl-1-amido (4b), bis[(3-triethoxysilyl)propyl]amido (4c), bis[(3-trimethoxysilyl)propyl]amido (4d), 3-[diethoxy(methyl)silyl]propyl-1-amido (4e), 24(3-(trimethoxysilyl)propyl) amino)ethyl-1-amido (4f), 2-((3-(triethoxysilyl)propyl) amino)ethyl-1-amido (4g), 9-(trimethoxysilyl)-3,6-diazanonane-1-amido (4h), phenyl((trimethoxysilyl)methyl) amido (4i), phenyl(3-(trimethoxysilyl)propyl)amido (4j), and 2-((3-(dimethoxy(methyl)silyl)propyl)amino)ethyl-1-amido (4k), and 4-(3-(dimethoxy(methyl)silyl)propyl)piperazin-1-ido (4l).

$$NH(CH_2)_3Si(OMe)_3 \qquad (4a)$$

$$NH(CH_2)_3Si(OEt)_3 \qquad (4b)$$

$$N[(CH_2)_3Si(OEt)_3]_2 \qquad (4c)$$

$$N[(CH_2)_3Si(OMe)_3]_2 \qquad (4d)$$

$$NH(CH_2)_3Si(OEt)_2(Me) \qquad (4e)$$

$$NH(CH_2)_2NH(CH_2)_3Si(OMe)_3 \qquad (4f)$$

$$NH(CH_2)_2NH(CH_2)_3Si(OEt)_3 \qquad (4g)$$

$$NH(CH_2)_2NH(CH_2)_2NH(CH_2)_3Si(OMe)_3 \qquad (4h)$$

$$NPh(CH_2)Si(OMe)_3 \qquad (4i)$$

$$NPh(CH_2)_3Si(OMe)_3 \qquad (4j)$$

$$NH(CH_2)_2NH(CH_2)_3SiMe(OMe)_2 \qquad (4k)$$

$$N(CH_2CH_2)_2N(CH_2)_3SiMe(OMe)_2 \qquad (4l)$$

Titanium amides of this type are easily prepared from chlorine titanates and suitable ligand precursors. Preferred ligand precursors are the alkali metal salts, in particular the lithium salts, of primary or secondary amines. The reaction proceeds according to the following equation:

$$TiL^1{}_nL^2{}_m + m\ NX_2M \rightarrow TiL^1{}_n(NX_2)_m + m\ ML^2,$$

where $L^2$ is a halide, in particular Cl, and M is an alkali metal such as Na, K, Li, or an alkaline earth metal such as Mg (in which case M=MgX, where X=Cl, Br, or I), preferably with Li. n and m are defined as above for formula (2). These amide salts are synthesized in situ by deprotonation of the corresponding primary or secondary amines with alkali metals or organometallic reagents. In preferred embodiments, n=3, m=1, $L^2$=Cl, $L^1$=OR$^4$, and M=Li.

In further embodiments, the at least one titanium compound is a titanium compound of formula (5), $$Ti(OR^4)_3(R^5) \qquad (5),$$

where each $R^4$ is independently $C_{1-8}$ alkyl, in particular for ethyl, isopropyl, or n-butyl; and $R^5$ is $C_{1-10}$ alkyl, cyclopentadienyl, or aryl, in particular for methyl.

Titanium compounds of this type are easily prepared from chlorine titanates and suitable ligand precursors, analogously to the titanium amides described above. Preferred ligand precursors are organometallic alkyl, cyclopentadienyl, or aryl compounds. The reaction proceeds according to the following equation:

$$TiL^1{}_nL^2{}_m + m\ R^5M \rightarrow TiL^1{}_nR^5{}_m + m\ ML^2,$$

where $L^2$ is a halide, in particular Cl, and M is an alkali metal such as Na, K, Li, or an alkaline earth metal such as Mg (in which case M=MgX, where X=Cl, Br, or I), preferably with Li. n and m are defined as above for formula (2). In preferred embodiments, n=3, m=1, $L^2$=Cl, $L^1$=OR$^4$, M=Li, and $R^5$ is defined as above.

In preferred embodiments, the composition also contains at least one compound c) which has a hydrolyzable silicon-containing group and a molecular weight in the range of 100 to 1000 g/mol. This compound is used as a crosslinking agent, and in addition to the hydrolyzable silicon-containing group may contain further functional groups. The compound may be a silane coupling agent.

This type of coupling agent may be used as a tackifier, as an agent which influences the physical properties, as a drying agent, as a dispersion aid, or as a filler or the like. In particular, such a silane coupling agent can act as an adhesion promoter and increase the adhesion to various surfaces, for example glass, aluminum, stainless steel, zinc, copper, mortar, PVC, acrylic resins, polyester, polyethylene, polypropylene, and polycarbonate. Such a silane coupling agent may include reactive silicon-containing groups which may be defined analogously to the groups described above in conjunction with polymer component a). Alternatively, the groups may also be those of formula (7):

$$-(SI(R^1)_{2-e}(X)_3-O)_k-SI(R^1)_{3-d}X_d \qquad (7),$$

where $R^1$ and X are each independently defined as above for formula (1), and e is 0, 1, or 2 and d is 0, 1, 2, or 3, where d and e are both not 0, and k is 0 or an integer from 1 to 19, where d is not 0 when k is 0.

Compound c) may contain further functional groups, including but not limited to primary, secondary, or tertiary amino groups, mercapto groups, epoxy groups, carboxyl groups, vinyl groups, isocyanate groups, isocyanurate groups, halogens, and the like.

Specific examples of these coupling agents include but are not limited to silanes containing Isocyanate groups, such as gamma-isocyanate propyltrimethoxysilane, gamma-isocyanate propyltriethoxysilane, gamma-Isocyanate propylmethyldiethoxysilane, gamma-isocyanate propylmethyldimethoxysilane, (isocyanate methyl)trimethoxysilane, (isocyanate methyl)methyldimethoxysilane, (isocyanate methyl)triethoxysilane, and (isocyanate methyl)diethoxymethylsilane; silanes containing amino groups, such as gamma-aminopropyltrimethoxysilane, gamma-aminopropyltriethoxysilane, gamma-aminopropyltriisopropoxysilane, gamma-aminopropylmethyldimethoxysilane, gamma-aminopropylmethyldiethoxysilane, gamma-(2-anninoethyl)aminopropyltrimethoxysilane, gamma-(2-aminoethyl)aminopropylmethyldimethoxysilane, gamma-(2-aminoethyl)aminopropyltriethoxysilane, gamma-(2-aminoethyl)aminopropylmethyldiethoxysilane, gamma-(2-aminoethyl)aminopropyltriisopropoxysilane, gamma-(6-aminohexyl)aminopropyltrinnethoxysilane, 3-(N-ethylamino)-2-methylpropyltrimethoxysilane, gamma-ureidopropyltrimethoxysilane, gamma-ureidopropyltriethoxysilane, N-phenyl-gamma-aminopropyltrimethoxysilane, N-benzyl-gamma-aminopropyltrimethoxysilane, N-vinylbenzyl-gamma-aminopropyltriethoxysilane, N-cyclohexylaminomethyltriethoxysilane, N-cyclohexylaminomethyldiethoxymethylsilane, N-phenylaminomethyltrimethoxysilane, (2-aminoethyl)aminomethyltrimethoxysilane, and N,N'-bis[3-(trimethoxysilyl)propyl]ethylenediamine; silanes of the ketimine type, such as N-(1,3-dimethylbutylidene)-3-(triethoxysilyl)-1-propanamine; silanes containing mercapto groups, such as gamma-mercaptopropyltrimethoxysilane, gamma-mercaptopropyltriethoxysilane, gamma-mercaptopropylmethyldimethoxysilane, gamma-mercaptopropylmethyldiethoxysilane, mercaptomethyltrimethoxysilane, and mercaptomethyltriethoxysilane; silanes containing epoxy groups, such as gamma-glycidoxypropyltrimethoxysilane, gamma-glycidoxypropyltriethoxysilane, gamma-glycidoxypropylmethyldimethoxysilane, beta-(3,4-epoxycyclohexyl)ethyltrimethoxysilane, and beta-(3,4-epoxycyclohexyl)ethyltriethoxysilane; carboxysilanes, such as beta-carboxyethyltriethoxysilane, beta-carboxyethylphenylbis(2-methoxyethoxy)silane, and N-beta-(carboxymethyl)aminoethyl-gamma-aminopropyltrimethoxysilane; silanes containing unsaturated groups of the vinyl type, such as vinyltrimethoxysilane, vinyltriethoxysilane, gamma-methacryloyloxypropylmethyldimethoxysilane, gamma-acryloyloxypropyltriethoxysilane, and methacryloyloxymethyltrimethoxysilane; silanes containing halogen, such as gamma-chloropropyltrimethoxysilane; and isocyanurate silanes, such as tris(3-trimethoxysilylpropyl)isocyanurate. In addition, partially condensed products or reaction products of the above-mentioned silanes may be used. Aminosilanes are particularly preferred within the scope of the present invention.

Examples of compounds c) which contain no additional functional groups include tetraalkoxysilanes (tetraalkylsilicates), such as tetramethoxysilane, tetraethoxysilane, ethoxytrimethoxysilane, dimethoxydiethoxysilane, methoxytriethoxysilane, tetra-n-propoxysilane, tetra-isopropoxysilane, tetra-n-butoxysilane, tetra-isobutoxysilane, and tetra-t-butoxysilane; trialkoxysilanes, such as methyltrimethoxysilane, methyltriethoxysilane, methyltriisopropoxysilane, methyltriphenoxysilane, ethyltrimethoxysilane, butyltrimethoxysilane, and phenyltrimethoxysilane; dialkoxysilanes, such as dimethyldimethoxysilane, diethyldimethoxysilane, and diphenyldimethoxysilane; monoalkoxysilanes, such as trimethylmethoxysilane and triphenylmethoxysilane; alkylisopropenoxysilanes, such as dimethyldiisopropenoxysilane and methyltriisopropenoxysilane; and the partially hydrolyzed condensates of these silanes.

A further subject matter of the present invention is a preparation which contains the curable composition according to the invention. According to an another preferred embodiment of the preparation according to the invention, the preparation also contains at least one compound selected from the group comprising plasticizers, stabilizers, antioxidants, fillers, reactive diluents, drying agents, adhesion promoters, UV stabilizers, rheological aids, and/or solvents. The titanium catalyst described above or mixtures of various titanium catalysts, i.e., titanium compound b), may be used in the preparation in a quantity of 0.001 to approximately 5% by weight, preferably 0.001 to 1.5% by weight, based on the total weight of the preparation.

The quantity of reactive polymer a) In the preparations described herein may be 30 to 90% by weight, based on the total weight of the preparation. The quantity of crosslinking agent c) may be 2.5 to 7% by weight, based on the total weight of the preparation. Adhesion promoters may be used in quantities of 0 to 5% by weight, based on the total weight of the preparation.

The curable compositions and preparations described herein may be used as adhesives and sealants. This type of use is likewise part of the invention.

It is conceivable that the viscosity of the adhesive or sealant according to the invention may be too high for certain applications. The viscosity may then generally be easily and suitably reduced or adjusted by using a reactive diluent, without resulting in demixing effects (for example, plasticizer migration) in the cured compound.

The reactive diluent preferably has at least one functional group which reacts with moisture or atmospheric oxygen, for example, after application. Examples of such groups are silyl groups, isocyanate groups, vinylically unsaturated groups, and multiply unsaturated systems.

All compounds which are miscible with the adhesive or sealant with reduction of the viscosity and which have at least one group that is reactive with the binder may be used as reactive diluent.

The viscosity of the reactive diluent is preferably less than 20,000 mPas, particularly preferably approximately 0.1-6000 mPas, very particularly preferably 1-1000 mPas (Brookfield RVT, 23° C., spindle 7, 10 rpm).

The following materials, for example, may be used as reactive diluent: polyalkylene glycols reacted with isocyanatosilanes (for example, Synalox 100-50B, DOW), carbamatopropyltrimethoxysilane, alkyltrimethoxysilanes and alkyltriethoxysilanes such as methyltrimethoxysilane, methyltriethoxysilane, and vinyltrimethoxysilane (XL 10, Wacker), vinyltriethoxysilane, phenyltrimethoxysilane, phenyltriethoxysilane, octyltrimethoxysilane, tetraethoxysilane, vinyldimethoxymethylsilane (XL12, Wacker), vinyltriethoxysilane (GF56, Wacker), vinyltriacetoxysilane (GF62, Wacker), isooctyltrimethoxysilane (10 Trimethoxy), isooctyltriethoxysilane (10 Triethoxy, Wacker), N-trimethoxysilylmethyl-O-methylcarbamate (XL63, Wacker), N-dimethoxy(methyl)silylmethyl-O-methylcarbamate (XL65, Wacker), hexadecyltrimethoxysilane, 3-octanoylthio-1-propyltriethoxysilane, and partial hydrolysates of these compounds.

The following polymers from Kaneka Corp. are likewise usable as reactive diluent: MS S203H, MS S303H, MS SAT 010, and MS SAX 350.

Silane-modified polyethers which are derived, for example, from the reaction of isocyanatosilane with Synalox types may likewise be used.

Also usable as reactive diluent are polymers which are producible from an organic backbone by grafting with a vinylsilane or by reacting polyol, polyisocyanate, and alkoxysilane.

A polyol is understood to mean a compound which may contain one or more hydroxyl (OH) groups in the molecule. The OH groups may be primary as well as secondary.

Examples of suitable aliphatic alcohols include ethylene glycol, propylene glycol, and higher glycols, as well as other polyfunctional alcohols. The polyols may additionally contain further functional groups such as esters, carbonates, and amides.

For producing the reactive diluents preferred according to the invention, the corresponding polyol component in each case is reacted with an at least difunctional isocyanate. As at least difunctional isocyanate, any isocyanate having at least two isocyanate groups is suitable in principle; however, within the scope of the present invention, compounds having two to four isocyanate groups, in particular two isocyanate groups, are generally preferred.

The compound which is present as reactive diluent within the scope of the present invention preferably has at least one alkoxysilyl group, with the di- and trialkoxysilyl groups being preferred among the alkoxysilyl groups.

Suitable as polyisocyanates for producing a reactive diluent, for example, are ethylene diisocyanate, 1,4-tetramethylene diisocyanate, 1,4-tetramethoxybutane diisocyanate, 1,6-hexamethylene diisocyanate (HDI), cyclobutane-1,3-diisocyanate, cyclohexane-1,3- and -1,4-diisocyanate, bis(2-isocyanatoethyl)fumarate, and mixtures of two or more thereof, 1-isocyanato-3,3,5-trimethyl-5-isocyanatomethylcyclohexane (isophorone diisocyanate, IPDI), 2,4- and 2,6-hexahydrotoluylene diisocyanate, hexahydro-1,3- or -1,4-phenylene diisocyanate, benzidine diisocyanate, naphthalene-1,5-diisocyanate, 1,6-diisocyanato-2,2,4-trimethylhexane, 1,6-diisocyanato-2,4,4-trimethylhexane, xylylene diisocyanate (XDI), tetramethylxylylene diisocyanate (TMXDI), 1,3- and 1,4-phenylene diisocyanate, 2,4- or 2,6-toluylene diisocyanate (TDI), 2,4'-diphenylmethane diisocyanate, 2,2'-diphenylmethane diisocyanate, or 4,4'-diphenylmethane diisocyanate (MDI) or the partially or completely hydrogenated cycloalkyl derivatives thereof, for example completely hydrogenated MDI (H12-MDI), alkyl-substituted diphenylmethane diisocyanates, for example mono-, di-, tri-, or tetraalkyldiphenylmethane diisocyanate and partially or completely hydrogenated cycloalkyl derivatives thereof, 4,4'-diisocyanatophenylperfluoroethane, phthalic acid-bis-isocyanatoethyl ester, 1-chloromethylphenyl-2,4- or -2,6-diisocyanate, 1-bromomethylphenyl-2,4- or -2,6-diisocyanate, 3,3-bis-chloromethyl ether-4,4'-diphenyl diisocyanate, sulfur-containing diisocyanates which are obtainable by reacting 2 mol diisocyanate with 1 mol thiodiglycol or dihydroxydihexylsulfide, the di- and triisocyanates of dimer and trimer fatty acids, or mixtures of two or more of the stated diisocyanates.

Trivalent or higher-valent isocyanates, which are obtainable, for example, by oligomerization of diisocyanates, in particular by oligomerization of the above-mentioned isocyanates, may likewise be used as polyisocyanates. Examples of such trivalent and higher-valent polyisocyanates are the triisocyanurates of HDI or IPDI or mixtures thereof or mixed triisocyanurates thereof, and polyphenylmethylene polyisocyanate, which is obtainable by phosgenation of aniline-formaldehyde condensation products.

Solvents and/or plasticizers may be used in addition to or instead of a reactive diluent for reducing the viscosity of the preparation according to the invention.

Aliphatic or aromatic hydrocarbons, halogenated hydrocarbons, ketones, ethers, esters, ester alcohols, keto alcohols, keto ethers, keto esters, and ether esters are suitable as solvent.

The preparation according to the invention may also contain hydrophilic plasticizers. These are used for improving the moisture absorption, and thus for enhancing the reactivity at low temperatures. Suitable as plasticizers, for example, are esters of abietic acid, adipic acid esters, azelaic acid esters, benzoic acid esters, butyric acid esters, acetic acid esters, esters of higher fatty acids containing approximately 8 to approximately 44 C atoms, esters of epoxidized fatty acids, fatty acid esters and fats, glycolic acid esters, phosphoric acid esters, phthalic acid esters, esters of linear or branched alcohols containing from 1 to 12 C atoms, propionic acid esters, sebacic acid esters, sulfonic acid esters, thiobutyric acid esters, trimellitic acid esters, citric acid esters, and esters based on nitrocellulose and polyvinyl acetate, and mixtures of two or more thereof.

Suitable among the phthalic acid esters, for example, are dioctyl phthalate, dibutyl phthalate, diisoundecyl phthalate, or butylbenzyl phthalate, and among the adipates are dioctyl adipate, diisodecyl adipate, diisodecyl succinate, dibutyl sebacate, or butyl oleate.

Likewise suitable as plasticizer are the pure or mixed ethers of monofunctional, linear, or branched $C_{4-16}$ alcohols or mixtures of two or more different ethers of such alcohols, for example dioctyl ether (obtainable as Cetiol OE, Cognis Deutschland GmbH, Düsseldorf).

Polyethylene glycols which are closed by a terminal group are also suitable as plasticizer. Examples are polyethylene glycol or polypropylene glycol di-$C_{1-4}$ alkyl ethers, in particular the dimethyl or diethyl ethers of diethylene glycol or dipropylene glycol, and mixtures of two or more thereof.

Particularly preferred as plasticizer, however, are polyethylene glycols which are closed by a terminal group, such as polyethylene glycol dialkyl ethers or polypropylene glycol dialkyl ethers, wherein the alkyl radical is one to four C atoms, and in particular the dimethyl and diethyl ethers of diethylene glycol and dipropylene glycol. In particular, acceptable curing, even under fairly unfavorable application conditions (low humidity, low temperature) is achieved with dimethyldiethylene glycol. Reference is made to the relevant literature in technical chemistry for further particulars concerning plasticizers.

Likewise suitable as plasticizer within the scope of the present invention are diurethanes, which may be produced, for example, by reacting diols having OH end groups with monofunctional isocyanates, by selecting the stoichiometry in such a way that essentially all free OH groups react. Any excess isocyanate may subsequently be removed, for example, by distillation from the reaction mixture. Another method for producing diurethanes is to react monofunctional alcohols with diisocyanates, with preferably all NCO groups reacting.

The preparation according to the invention may also contain up to approximately 20% by weight of customary adhesion promoters (tackifiers). Suitable as adhesion promoters, for example, are resins, terpene oligomers, coumarone/indene resins, aliphatic petrochemical resins, and modified phenolic resins. Suitable within the scope of the present invention, for example, are hydrocarbon resins which are obtained by polymerization of terpenes, primarily α- or β-pinene, dipentene, or limonene. The polymerization of these monomers generally takes place cationically with initiation with Friedel-Crafts catalysts. The terpene resins also include, for example, copolymers of terpenes and other monomers, for example styrene, a-methylstyrene, isoprene, and the like. The stated resins are used, for example, as adhesion promoters for contact adhesives and coating materials. Likewise suited are terpene phenolic resins, which are produced by acid-catalyzed addition of phenols to terpenes or colophony. Terpene phenolic resins are soluble in most organic solvents and oils and miscible with other resins, waxes, and rubber. Likewise suitable as additives within the scope of the present invention are colophony resins and derivatives thereof, for example esters thereof.

Furthermore, the preparation according to the invention may additionally contain up to approximately 7% by weight, in particular up to approximately 5% by weight, of antioxidants.

The preparation according to the invention may contain up to approximately 2% by weight, preferably approximately 1% by weight, of UV stabilizers. The so-called hindered amine light stabilizers (HALS) are particularly suitable as UV stabilizers. Within the scope of the present invention, it is preferred to use a UV stabilizer which bears a silyl group and which is incorporated into the end product during crosslinking and curing. The products Lowilite 75 and Lowilite 77 (Great Lakes, US) are particularly suited for this purpose. In addition, benzotriazoles, benzophenones, benzoates, cyanoacrylates, acrylates, sterically hindered phenols, phosphorus, and/or sulfur may also be added.

It is often expedient to further stabilize the preparations according to the invention against penetrating moisture by use of drying agents in order to further extend the shelf life.

Such an improvement in the shelf life may be achieved, for example, by the use of drying agents. All compounds which react with water to form a group that is inert with respect to the reactive groups present in the composition, and which in the process preferably experience little change in their molecular weight, are suitable as drying agent. Furthermore, the reactivity of the drying agents with respect to moisture that has penetrated into the composition must be higher than the reactivity of the groups of the silyl group-bearing polymer according to the invention present in the preparation.

Isocyanates, for example, are suitable as drying agent.

Silanes are advantageously used as drying agent. Examples are vinylsilanes such as 3-vinylpropyltriethoxysilane, oxime silanes such as methyl-O,O',O''-butan-2-one-trioximosilane or O,O',O'',O'''-butan-2-one-tetraoximosilane (CAS Nos. 022984-54-9 and 034206-40-1), or benzamidosilanes such as bis(N-methylbenzamido)methylethoxysilane (CAS No. 16230-35-6) or carbamatosilanes such as carbamatomethyltrimethoxysilane. However, the use of methyl-, ethyl-, or vinyltrimethoxysilane or tetramethyl- or tetraethylethoxysilane is also possible. With regard to efficiency and cost, vinyltrimethoxysilane and tetraethoxysilane are particularly preferred here.

Likewise suitable as drying agent are the above-mentioned reactive diluents, provided that they have a molecular weight (Ma) of less than approximately 5,000 g/mol and have end groups whose reactivity with respect to penetrated moisture is at least as high as, preferably higher than, the reactivity of the reactive groups of the silyl group-bearing polymer according to the invention.

Lastly, alkyl orthoformates or orthoacetates, for example methyl or ethyl orthoformate, methyl or ethyl orthoacetate, may also be used as drying agent.

The adhesives and sealants according to the invention generally contain approximately 0 to approximately 6% by weight of drying agent.

The preparation according to the invention may additionally contain fillers. Suitable examples here are chalk, lime powder, precipitated and/or pyrogenic silicic acid, zeolites, bentonites, magnesium carbonate, diatomaceous earth, alumina, clay, talc, titanium oxide, iron oxide, zinc oxide, sand, quartz, flint, mica, glass powder, and other ground mineral substances. In addition, organic fillers may also be used, in particular carbon black, graphite, wood fiber, wood flour, sawdust, cellulose, cotton, pulp, wood chips, chopped straw, and chaff. Moreover, short fibers such as glass fiber, glass filament, polyacrylonitrile, carbon fiber, Kevlar fiber, or also polyethylene fiber may be added. Powdered aluminum is likewise suitable as filler.

The pyrogenic and/or precipitated silicic acids advantageously have a BET surface area of 10 to 90 m²/g. During use, they do not cause an additional increase in the viscosity of the preparation according to the invention, but contribute to strengthening of the cured preparation.

It is likewise conceivable to use pyrogenic and/or precipitated silicic acids having a larger BET surface area, advantageously 100-250 m²/g, in particular 110-170 m²/g, as filler. Due to the larger BET surface area, the same effect, for example strengthening the cured preparation, may be obtained at a lower weight fraction. Further substances may thus be used to improve the preparation according to the invention with regard to other requirements.

Furthermore, hollow spheres having a mineral shell or a plastic shell are suitable as filler. These may be, for example, hollow glass spheres which are commercially available under the trade name Glass Bubbles®. Hollow spheres based on plastic, for example Expancel® or Dualite®, are described in EP 0 520 426 B1, for example. These are composed of inorganic or organic substances, each having a diameter of 1 mm or less, preferably 500 µm or less.

For some applications, fillers are preferred which impart thixotropy to the preparations. Such fillers are also described as rheological aids, for example hydrogenated castor oil, fatty acid amides, or swellable plastics such as PVC. To allow them to be easily pressed out of a suitable dosing device (a tube, for example), such preparations have a viscosity of 3000 to 15,000 mPas, preferably 40,000 to 80,000 mPas, or also 50,000 to 60,000 mPas.

The fillers are preferably used in a quantity of 1 to 80% by weight, based on the total weight of the preparation.

The preparation according to the invention is produced according to known methods by intimately mixing the components in suitable dispersion units, for example a high-speed mixer.

A further subject matter of the present invention relates to use of the composition according to the invention or the preparation according to the invention as an adhesive, sealant, or filling compound, and for producing molded parts. A further field of application of the compositions according to the inventions is use as plugging, hole-filling, or spackling compound.

The compositions and preparations according to the invention are thus suitable for adhesively bonding plastics, metals, glass, ceramic, wood, wood-based materials, paper, paper-based materials, rubber, and textiles, for gluing floors, sealing building elements, windows, wall and floor coverings, and jointing in general. In this regard, the materials in each case may be adhesively bonded to themselves or with any other of the stated materials.

In a further aspect, the invention also relates to the titanium compounds of formula (6)

where each $R^4$ is independently $C_{1-8}$ alkyl, in particular for ethyl, isopropyl, or n-butyl; X is hydrogen, $C_{1-20}$ alkyl, or aryl, wherein the alkyl radical may optionally contain one or more nitrogen atoms, or a silicon-containing organic group of formula —$(CH2)_p$—$Si(Alk)_q(OAlk)_r$, where p is an integer from 0 to 9, q is 0, 1, or 2, r is 1, 2, or 3, where q+r=3, and Alk is a $C_{1-4}$ alkyl group, in particular methyl or ethyl; and X' is a silicon-containing organic group of formula —$(CH_2)_p$—$Si(Alk)_q(OAlk)_r$, where p is an integer from 1 to 9, in particular 3, q is 0, 1, or 2, in particular 0, r is 1, 2, or 3, in particular 3, where q+r=3, and Alk is a $C_{1-4}$ alkyl group, in particular methyl or ethyl.

In preferred embodiments of these titanium compounds of formula (6), the ligand of formula $(NX_2)$ is a ligand as defined above for formulas (2) and (4), i.e., a ligand which is obtainable by coupling an aminosilane to the titanium. Examples of such ligands include but are not limited to bis(trialkylsilyl)amido, such as bis(trimethylsilyl)amido, trialkoxysilaneamido, and bis(trialkoxysilane)amido, in particular trialkoxysilanealkylamido and bis(trialkoxysilanealkyl)amido, such as 3-(triethoxysilyl)propyl-1-amido (4a), 3-(trimethoxysilyl)propyl-1-amido (4b), bis[(3-triethoxysilyl)propyl]amido (4c), bis[(3-trimethoxysilyl)propyl]amido (4d), 3-[diethoxy(methyl)silyl]propyl-1-amido (4e), 2-((3-(trimethoxysilyl)propyl)amino)ethyl-1-amido (4f), 2-((3-(triethoxysilyl)propyl)amino)ethyl-1-amido (4g), 9-(trimethoxysilyl)-3,6-diazanonane-1-amido (4h), phenyl ((trimethoxysilyl)methyl)amido (4i), phenyl(3-(trimethoxysilyl)propyl)amido (4j), 2-((3-(dimethoxy(methyl)silyl)propyl)amino)ethyl-1-amido (4k).

N[(CH$_2$)$_3$Si(OEt)$_3$]$_2$     (4c)

N[(CH$_2$)$_3$Si(OMe)$_3$]$_2$     (4d)

NH(CH$_2$)$_3$Si(OEt)$_2$(Me)     (4e)

NH(CH$_2$)$_2$NH(CH$_2$)$_3$Si(OMe)$_3$     (4f)

NH(CH$_2$)$_2$NH(CH$_2$)$_3$Si(OEt)$_3$     (4g)

NH(CH$_2$)$_2$NH(CH$_2$)$_2$NH(CH$_2$)$_3$Si(OMe)$_3$     (4h)

NPh(CH$_2$)Si(OMe)$_3$     (4i)

NPh(CH$_2$)$_3$Si(OMe)$_3$     (4j)

NH(CH$_2$)$_2$NH(CH$_2$)$_3$SiMe(OMe)$_2$     (4k)

N(CH$_2$CH$_2$)$_2$N(CH$_2$)$_3$SiMe(OMe)$_2$     (4l)

Lastly, the invention further relates to the use of these titanium compounds as catalyst, in particular as condensation catalyst, for curing a silicon-containing polymer. During this curing, the reactive silicon-containing groups are cross-linked to form siloxane bonds.

The following examples are used to explain the invention; however, the invention is not limited thereto.

EXAMPLES

Example 1:

Bis(trimethylsilyl)amido-tris(isopropoxy)titanium

The following method is based on the method disclosed in *J. Chem. Soc. A*, 1968, 1940-1945, and has been appropriately adapted for synthesizing the catalysts described herein.

3 mL of a 2.5 M solution of n-BuLi (n-butyllithium) was diluted in 40 mL dry n-hexane in a Schlenk flask under an argon atmosphere and cooled to −20° C. 1.29 g (8.02 mmol) hexamethyldisilazane (HMDS) was added dropwise to the cooled solution over a period of 30 minutes. After addition was complete, the mixture was stirred and 2.1 g (8.06 mmol) tris(isopropoxy)titanium chloride was added dropwise. The mixture was heated slowly to room temperature, and the resulting precipitate was separated and washed with dry n-hexane. The combined organic extracts were concentrated under vacuum and the oily crude product was distilled under vacuum to obtain the product as a clear, colorless liquid (2.5 g, 7.68 mmol, 95% yield).

The product was used as a catalyst in the following formulations.

TABLE 1

Formulation 1 (alkoxy silicone without adhesion promoter)

| Raw material | Parts by weight |
|---|---|
| α,ω-di-dimethoxyvinyl-terminated polydimethylsiloxane having a viscosity of 80,000 cST (See U.S. Pat. No. 5,663,269 for exact production specification) | 70.94 |
| Polydimethylsiloxane having a viscosity of 100 cST | 16.76 |
| Highly dispersed silicic acid (Aerosil R104) | 11 |
| Catalyst | 1.3 |

TABLE 2

Formulation 2 (alkoxy silicone with adhesion promoter)

| Raw material | Parts by weight |
|---|---|
| α,ω-di-dimethoxyvinyl-terminated polydimethylsiloxane having a viscosity of 50,000 cST (See US 2003/0216536 for exact production specification) | 48.3 |
| Chalk, calcium carbonate | 45.2 |
| Highly dispersed silicic acid (Aerosil R974) | 4.4 |
| Aminopropyltrimethoxysilane | 0.8 |
| Catalyst | 0.17 |

TABLE 3

Formulation 3 (oxime silicone with adhesion promoter)

| Raw material | Parts by weight |
|---|---|
| α,ω-dihydroxy-terminated polydimethylsiloxane having a viscosity of 80,000 | 59.75 |
| Mineral oil (G3H) | 24.75 |
| Methyltris(methylisobutylketoxime)silane | 1.7 |
| Methyltris(methylethylketoximo)silane | 2.1 |
| Vinyltris(methylethylketoxime)silane | 0.5 |
| Highly dispersed silicic acid (Aerosil 150) | 10 |
| Aminopropyltriethoxysilane | 1.15 |
| Catalyst | 0.05 |

Example 2:

Methyltris(isopropoxy)titanium

The production of methyl-tris(isopropoxy)titanium is based on the method disclosed in *J. Organomet. Chem* 1974, 74, 85-90.

The product was used as a catalyst in the following formulations.

TABLE 4

Formulation 4 (alkoxy silicone without adhesion promoter)

| Raw material | Parts by weight |
|---|---|
| α,ω-di-dimethoxyvinyl-terminated polydimethylsiloxane having a viscosity of 80,000 cST (See U.S. Pat. No. 5,663,269 A for exact production specification) | 70.94 |
| Polydimethylsiloxane having a viscosity of 100 cST | 16.76 |
| Highly dispersed silicic acid (Aerosil R104) | 11 |
| Catalyst | 1.3 |

TABLE 5

Formulation 5 (alkoxy silicone with adhesion promoter)

| Raw material | Parts by weight |
|---|---|
| α,ω-di-dimethoxyvinyl-terminated polydimethylsiloxane having a viscosity of 50,000 cST (See US 2003/0216536 for exact production specification) | 49.43 |
| Chalk, calcium carbonate | 45.2 |
| Highly dispersed silicic acid (Aerosil R974) | 4.4 |
| Aminopropyltrimethoxysilane | 0.8 |
| Catalyst | 1.3 |

TABLE 6

Formulation 6 (oxime silicone with adhesion promoter)

| Raw material | Parts by weight |
|---|---|
| α,ω-dihydroxy-terminated polydimethylsiloxane having a viscosity of 80,000 | 59.75 |
| Mineral oil (G3H) | 24.75 |
| Methyltris(methylisobutylketoxime)silane | 1.7 |
| Methyltris(methylethylketoximo)silane | 2.1 |
| Vinyltris(methylethylketoxime)silane | 0.5 |
| Highly dispersed silicic acid (Aerosil 150) | 10 |
| Aminopropyltriethoxysilane | 1.15 |
| Catalyst | 0.05 |

Example 3:

Adhesion Test and Mechanical

Measurement of Skin Formation Time

The determination of the skin formation time is carried out under standard climate conditions (23+/−2° C., relative humidity 50+/−5%). The temperature of the sealant must be 23+/−2° C., with the sealant stored for at least 24 h beforehand in the laboratory. The sealant is applied to a sheet of paper and spread out with a putty knife to form a skin (thickness approximately 2 mm, width approximately 7 cm). The stopwatch is started immediately. At intervals, the surface is touched lightly with the fingertip and the finger is pulled away, with sufficient pressure on the surface that an impression remains on the surface when the skin formation time is reached. The skin formation time is reached when sealing compound no longer adheres to the fingertip. The skin formation time is expressed in minutes.

Measurement of Shore A Hardness

The procedure is carried out in accordance with ISO 868.

Measurement of the Hardness Depth

A sealant strand having a height of 10 mm (+/−1 mm) and a width of 20 mm (+/−2 mm) is applied with an appropriate spatula to a plastic sheet. After storage for 24 hours under standard climate conditions (23+/−2° C., relative humidity 50+/−5%), a piece is cut from the strand, and the thickness of the cured layer is measured with a slide gauge. The hardness depth is expressed in mm/24 h.

Measurement of Mechanical Properties (Tensile Test)

The breaking strength, elongation at break, and tensile stress values (modulus of elasticity) are determined by the tensile test in accordance with DIN 53504.

Deviation from the norm: Dumbbell test specimens having the following dimensions are used as test pieces: thickness: 2 +/− 0.2 mm; width of web: 10+/−0.5 mm; length of web: approximately 45 mm; total length: 9 cm. The test is carried out under standard climate conditions (23+/−2° C., 50+/−5% relative humidity). The test is conducted after curing for 7 days.

Procedure: A film of the sealing compound 2 mm thick is spread out. The film is stored for 7 days under standard climate conditions, and the dumbbell test specimens are then punched out. Three dumbbell test specimens are produced for each determination. The test is carried out under standard climate conditions. The test pieces must be acclimatized (i.e., stored) beforehand for at least 20 minutes at the test temperature. Prior to the measurement, the thickness of the test pieces is measured at RT with a slide gauge at at least 3 locations; i.e., for the starting measurement length, preferably the ends and center of the dumbbell test specimens are measured. For elastic materials, it is recommended to take an additional measurement crosswise over the web. The average value is entered into the measurement program. The test pieces are clamped into the tensile testing machine in such a way that the longitudinal axis coincides with the mechanical axis of the tensile testing machine, and the largest possible surface area of the heads of the dumbbell test specimens is included without the web becoming jammed. The dumbbell test specimen is stretched to a pretensioning of <0.1 MPa at a feed rate of 50 mm/min. The curve of the change in force versus length is recorded at a feed rate of 50 mm/min.

Evaluation: The following values are taken from the measurement: breaking strength in [N/mm$^2$], elongation at break in [%], and modulus of elasticity at 100% elongation in [N/mm$^2$].

The results of the measurements are shown in Tables 7 and 8.

TABLE 7

Formulations 1 to 3 and comparative formulations V1, V2, V2', and V3

| Parameter | F1 | V1 | F2 | V2 | V2' | F3 | V3 |
|---|---|---|---|---|---|---|---|
| Skin formation time (min) | 33 | 46 | 8 | 20 | 24 | 15 | 17 |
| Shore A 7 d | 18 | 24 | 25 | 20 | 19 | 18 | 17 |
| Hardness depth (mm/24 h) | 2.25 | 2.62 | 3.08 | 2.11 | 2.65 | 2.74 | 3.11 |
| Modulus of elasticity at 100% (N/mm$^2$) | 0.33 | 0.50 | 0.52 | 0.36 | 0.59 | 0.32 | 0.24 |
| Breaking strength (N/mm$^2$) | 0.92 | 2.19 | 0.46 | 0.34 | 0.99 | 0.90 | 0.79 |
| Elongation at break (%) | 385 | 534 | 143 | 127 | 272 | 480 | 514 |

F1-F3 = formulation 1-3;
V1 = formulation 1 with 1.30% by weight tetra-n-butyl titanate instead of the titanium catalyst provided according to the invention;
V2 = formulation 2 with 0.17% by weight tetra-n-butyl titanate instead of the titanium catalyst provided according to the invention;
V2' = formulation 2 with 0.17% by weight tetra-isopropyl titanate instead of the titanium catalyst provided according to the invention;
V3 = formulation 3 with 0.05% by weight dibutyltin acetate instead of the titanium catalyst provided according to the invention.

TABLE 8

Formulations 4 to 6 and comparative formulations V4, V5, V6, V6', and V6"

| Parameter | F4 | V4 | F5 | V5 | F6 | V6 | V6' | V6" |
|---|---|---|---|---|---|---|---|---|
| Skin formation time (min) | 34 | 33 | 15 | 20 | 21 | 17 | 23 | 22 |
| Shore A 7 d | 18 | 18 | 36 | 20 | 16 | 17 | 18 | 20 |
| Hardness depth (mm/24 h) | 2.85 | 2.52 | 2.73 | 2.11 | 2.19 | 3.11 | 2.8 | 2.8 |
| Modulus of elasticity at 100% | 0.36 | 0.50 | 0.73 | 0.36 | 0.22 | 0.24 | 0.3 | 0.3 |

TABLE 8-continued

Formulations 4 to 6 and comparative formulations V4, V5, V6, V6', and V6"

| Parameter | F4 | V4 | F5 | V5 | F6 | V6 | V6' | V6" |
|---|---|---|---|---|---|---|---|---|
| Breaking strength (N/mm$^2$) | 0.89 | 2.19 | 0.97 | 0.34 | 0.85 | 0.79 | 0.8 | 0.7 |
| Elongation at break (%) | 315 | 534 | 196 | 127 | 600 | 514 | 315 | 281 |

F4-F6 = formulation 4-6;
V4 = formulation 4 with 0.17% by weight tetra-n-butyl titanate instead of the titanium catalyst provided according to the invention;
V5 = formulation 5 with 0.17% by weight tetra-n-butyl titanate instead of the titanium catalyst provided according to the invention;
V6 = formulation 6 with 0.05% by weight dibutyltin acetate instead of the titanium catalyst provided according to the invention.
V6' = formulation 6 with 0.05% by weight tetra-n-butyl titanate instead of the titanium catalyst provided according to the invention;
V6" = formulation 6 with 0.05% by weight tetra-isopropyl titanate instead of the titanium catalyst provided according to the invention.

What is claimed is:

1. Curable composition comprising:
   a) at least one polymer having at least one silicon-containing group of formula (1)

$$—Si(R^1)_k(Y)_{3-k} \quad (1),$$

where $R^1$ is a hydrocarbon radical containing 1 to 20 C atoms or a triorganosiloxane group of formula —O—Si$(R^2)_3$, where each $R^2$ is independently a hydrocarbon radical containing 1 to 20 C atoms;
   each Y is independently a hydroxy group or a hydrolyzable group; and
   k is 0, 1, or 2;
   b) at least one titanium compound of formula (4)

$$Ti(OR^4)_3(NX_2) \quad (4),$$

where each $R^4$ is independently $C_{1-8}$ alkyl; each X is independently hydrogen, $C_{1-20}$ alkyl, or $C_{6-20}$ aryl, wherein the alkyl radical optionally contains one or more nitrogen atoms, or a silicon-containing organic group of formula —(CH$_2$)$_p$—Si(Alk)$_q$(OAlk)$_r$, where p is an integer from 0 to 9, q and r in each case are 0, 1, 2, or 3, where q+r=3, and Alk is a $C_{1-4}$ alkyl group;
   c) optionally at least one compound which has a hydrolyzable silicon-containing group and a molecular weight in the range of 100 to 1000 g/mol.

2. Curable composition according to claim 1, characterized in that polymer a) has a polymer backbone that is selected from alkyd resins, (meth)acrylates and (meth)acrylamides and the salts thereof, phenolic resins, polyalkylenes, polyamides, polycarbonates, polyols, polyethers, polyesters, polyurethanes, vinyl polymers, siloxanes, and copolymers composed of at least two of the above-mentioned polymer classes.

3. Curable composition according to claim 1, characterized in that in the titanium compound of formula (4), the ligand of formula (NX$_2$) is selected from diethylamido, bis(trimethylsilyl)amido,

| | |
|---|---|
| 3-(trimethoxysilyl)propyl-1-amido | (4a), |
| 3-(triethoxysilyl)propyl-1-amido | (4b), |
| bis[(3-triethoxysily)propyl]amido | (4c), |
| bis[(3-trimethoxysilyl)propyl]amido (4d), | |
| 3-[diethoxy(methyl)silyl]propyl-1-amido | (4e), |
| 2-(3-(trimethoxysilyl)propyl)amino)ethyl-1-amido | (4f), |
| 2-((3-(triethoxysilyl)propyl)amino)ethyl-1-amido | (4g), |
| 9-(trimethoxysilyl)-3,6-diazanonane-1-amido | (4h), |
| phenyl((trimethoxysilyl)methyl)amido | (4i), |
| phenyl(3-(trimethoxysilyl)propyl)amido | (4j), |
| and 2-((3-(dimethoxy(methyl)silyl)propyl)amino) ethyl-1-amido | (4k) |
| NH(CH$_2$)$_3$Si(OMe)$_3$ | (4a) |
| NH(CH$_2$)$_3$Si(OEt)$_3$ | (4b) |
| N[CH$_2$)$_3$Si(OEt)$_3$]$_2$ | (4c) |
| N[(CH$_2$)$_3$Si(OMe)$_3$]2 | (4d) |
| NH(CH$_2$)$_3$Si(OEt)$_2$(Me) | (4e) |
| NH(CH$_2$)$_2$NH(CH$_2$)$_3$Si(OMe)$_3$ | (4f) |
| NH(CH$_2$)$_2$NH(CH$_2$)$_3$Si(OEt)$_3$ | (4g) |
| NH(CH$_2$)$_2$NH(CH$_2$)$_2$NH(CH$_2$)$_3$Si(OMe)$_3$ | (4h) |
| NPh(CH$_2$)Si(OMe)$_3$ | (4i) |
| NPh(CH$_2$)$_3$Si(OMe)$_3$ | (4j) |
| NH(CH$_2$)$_2$NH(CH$_2$)$_3$SiMe(OMe)$_2$ | (4k). |

4. Curable composition according to claim 1, characterized in that the composition as compound c) contains an aminosilane selected from bis(trimethylsilyl)amine, aminopropyltriethoxysilane, aminopropyltrimethoxysilane, bis[(3-triethoxysilyl)propyl]amine, bis[(3-trimethoxysily)propyl]amine, aminopropylmethyldiethoxysilane, aminoethylaminopropyltrimethoxysilane, aminoethylaminopropyltriethoxysilane, 3-[2-(2-aminoethylamino)ethylamino]propyltrimethoxysilane, phenylaminomethyltrimethoxysilane, aminoethylaminopropylmethyldimethoxysilane, 3-(N-phenylamino)propyltrimethoxysilane, 3-piperazinylpropylmethyldimethoxysilane, 3-(N,N-dimethylaminopropyl) aminopropylmethyldimethoxysilane, and combinations of two or more of the above-mentioned compounds.

5. The curable composition of claim 1 wherein Alk is methyl or ethyl.

6. The curable composition of claim 1 wherein the composition as compound c) contains an aminosilane.

7. Curable composition comprising:
a) at least one polymer having at least one silicon-containing group of formula (1)

$$—Si(R^1)_k(Y)_{3-k} \quad (1),$$

where $R^1$ is a hydrocarbon radical containing 1 to 20 C atoms or a triorganosiloxane group of formula —O—Si($R^2$)$_3$, where each $R^2$ is independently a hydrocarbon radical containing 1 to 20 C atoms;
each Y is independently a hydroxy group or a hydrolyzable group; and
k is 0, 1, or 2;
b) at least one titanium compound of formula (5)

$$Ti(OR^4)_3(R^5) \quad (5),$$

where each $R^4$ is independently $C_{1-8}$ alkyl; and $R^5$ is $C_{1-10}$ alkyl, cyclopentadienyl, or aryl;
c) optionally at least one compound which has a hydrolyzable silicon-containing group and a molecular weight in the range of 100 to 1000 g/mol.

8. The curable composition of claim 7 wherein the composition as compound c) contains an aminosilane.

9. The curable composition of claim 7 wherein each Y is independently selected from an oxime group or an alkoxy group.

10. The curable composition of claim 7 wherein each $R^4$ is independently selected from ethyl, isopropyl or n-butyl.

11. The curable composition of claim 7 wherein $R^5$ is methyl.

12. Titanium compound of formula (6)

$$Ti(OR^4)_3(NXX') \quad (6),$$

where each $R^4$ is independently $C_{1-8}$ alkyl;
X is hydrogen, $C_{1-20}$ alkyl, or aryl, wherein the alkyl radical optionally contains one or more nitrogen atoms, or a silicon-containing organic group of formula —(CH$_2$)$_p$—Si(Alk)$_q$(OAlk)$_r$, where p is an integer from 0 to 9, q is 0, 1, or 2, and r is 1, 2, or 3, where q+r=3, and Alk is a $C_{1-4}$ alkyl group; and
X' is a silicon-containing organic group of formula —(CH$_2$)$_p$—Si(Alk)$_q$(OAlk)$_r$, where p is an integer from 1 to 9, q is 0, 1, or 2, and r is 1, 2, or 3, where q+r=3, and Alk is a $C_{1-4}$ alkyl group.

13. A method of curing a silicon-containing polymer, comprising:
providing a curable silicon-containing polymer;
mixing the titanium compound according to claim 12 as catalyst with the curable silicon-containing polymer; and
curing the silicon-containing polymer by forming siloxane bonds.

14. The titanium compound of claim 12, wherein each $R^4$ is independently selected from ethyl, isopropyl or n-butyl.

15. The titanium compound of claim 12, wherein Alk is methyl or ethyl.

* * * * *